United States Patent [19]

Keogh

[11] Patent Number: 5,821,343
[45] Date of Patent: Oct. 13, 1998

[54] OXIDATIVE METHOD FOR ATTACHMENT OF BIOMOLECULES TO SURFACES OF MEDICAL DEVICES

[76] Inventor: James R. Keogh, 1201 Frank Ct., Maplewood, Minn. 55109

[21] Appl. No.: 635,187

[22] Filed: Apr. 25, 1996

[51] Int. Cl.$^6$ ............................. C07K 17/00; A61F 2/00; C12N 11/00; G01N 33/543
[52] U.S. Cl. ..................... 530/402; 424/422; 424/94.1; 435/174; 435/176; 435/177; 435/181; 436/518; 436/524; 436/528; 436/532; 530/810; 530/811; 530/812; 530/816
[58] Field of Search ................................. 435/174, 176, 435/177, 178, 180, 181; 530/810, 402, 811, 812, 816; 424/422, 94.1; 436/518, 524, 528, 532

[56] References Cited

U.S. PATENT DOCUMENTS

| 3,826,678 | 7/1974 | Hoffman et al. | 117/81 |
|---|---|---|---|
| 4,521,564 | 6/1985 | Solomon et al. | 525/54.1 |
| 4,600,652 | 7/1986 | Solomon et al. | 423/423.3 |
| 4,613,665 | 9/1986 | Larm | 536/20 |
| 4,642,242 | 2/1987 | Solomon et al. | 427/2 |
| 4,720,512 | 1/1988 | Hu et al. | 523/112 |
| 4,786,556 | 11/1988 | Hu et al. | 428/412 |
| 5,032,666 | 7/1991 | Hu et al. | 528/70 |
| 5,053,048 | 10/1991 | Pinchuk | 623/1 |
| 5,077,372 | 12/1991 | Hu et al. | 528/70 |
| 5,344,455 | 9/1994 | Keogh et al. | 623/11 |
| 5,362,852 | 11/1994 | Geoghegan | 530/345 |
| 5,545,213 | 8/1996 | Keogh et al. | 623/1 |

OTHER PUBLICATIONS

R.G. Dickinson et al., "A New Sensitive and Specific Test for the Detection of Aldehydes: Formation of 6–Mercapto–3–substituted–s–traizolo[4,3–b]–s–tetrazines", *Chem. Commun.*, 1719–1720 (1970).

K.F. Geoghegan et al., "Site–Directed Conjugation of Nonpeptide Groups to Peptides and Proteins via Periodate Oxidation of a 2–Amino Alcohol. Application to Modification at N–Terminal Serine", *Bioconjugate Chem.*, 3, 138–146 (1992).

A.S. Hoffman et al., Covalent Binding of Biomolecules to Radiation–Grafted Hydrogels on Inert Polymer Surfaces, *Trans. Am. Soc. Artif. Intern. Organs*, 18, 10–18 (1972).

S. Holmes et al., Amination of Ultra–high Strength Polyethylene using Ammonia Plasma, *Composites Science and Technology*, 38, 1–21 (1990).

Y. Ito et al., Materials for Enhancing Cell Adhesion by Immobilization of Cell–Adhesive Peptide, *J. Biomed. Mat. Res.*, 25, 1325–1337 (1991).

P.H. O'Farrell, High Resolution Two–Dimensional Electrophoresis of Proteins, *J. Biol. Chem.*, 250, 4007–4021, (1975).

*Primary Examiner*—David M. Naff
*Attorney, Agent, or Firm*—Thomas F. Woods; Harold R. Patton

[57] ABSTRACT

A method is provided for immobilizing a biomolecule coating on the surface of a medical device to obtain improved biocompatibility characteristics for contacting with tissue or body fluids such as blood. The method includes oxidizing a 2-aminoalcohol moiety of a material disposed on the surface with a periodate to form an aldehyde moiety, combining the aldehyde moiety with an amine moiety of a material to bond the aldehyde moiety to the amine moiety through an imine moiety and reacting the imine moiety with a reducing agent to form the coating immobilized on the surface by an amine linkage. Alternatively, the method includes providing on the surface a coating containing the materials having the 2-aminoalcohol moiety and the amine moiety, applying a periodate to oxidize the 2-aminoalcohol moiety to an aldehyde moiety, allowing the aldehyde moiety to react with the amine moiety through an imine moiety and reducing the imine moiety to form an amine linkage crosslinking the 2-aminoalcohol moiety to the amine moiety. The material containing the 2-aminoalcohol moiety or the amine moiety can be a biomolecule or a substrate surface of a medical device. Biomolecules such as proteins or peptides containing a 2-aminoalcohol moiety can be attached to an aminated surface or an aminated biomolecule can be attached to surface having a 2-aminoalcohol moiety.

10 Claims, No Drawings

OXIDATIVE METHOD FOR ATTACHMENT OF BIOMOLECULES TO SURFACES OF MEDICAL DEVICES

BACKGROUND OF THE INVENTION

For many years, a number of medical devices (e.g., pacemakers, vascular grafts, stents, heart valves, etc.) that contact bodily tissue or fluids of living persons or animals have been developed, manufactured, and used clinically. A major problem with such devices is that their surfaces tend to adsorb a layer of proteins from tissues and fluids such as tears, urine, lymph fluid, blood, blood products, and other fluids and solids derived from blood. The composition and organization of this adsorbed protein layer is thought to influence, if not control, further biological reactions. Adverse biological reactions such as thrombosis and inflammation can diminish the useful lifetime of many devices.

Implantable medical devices also tend to serve as foci for infection of the body by a number of bacterial species. These device-associated infections are promoted by the tendency of these organisms to adhere to and colonize the surface of the device. Consequently, it has been of great interest to physicians and the medical industry to develop surfaces of biomolecules that are less prone to promoting the adverse biological reactions that typically accompany the implantation of a device.

One approach for minimizing undesirable biological reactions associated with medical devices is to attach various biomolecules to their surfaces for the attachment and growth of a cell layer which the body will accept. Biomolecules such as growth factors, cell attachment proteins, and cell attachment peptides have been used for this purpose. In addition, biomolecules such as antithrombogenics, antiplatelets, anti-inflammatories, antimicrobials, and the like have also been used to minimize adverse biomaterial-associated reactions.

A number of approaches have been suggested to attach such biomolecules. These approaches typically require the use of coupling molecules such as glutaraldehyde, cyanogen bromide, p-benzoquinone, succinic anhydrides, carbodiimides, diisocyanates, ethyl chloroformate, dipyridyl disulphide, epichlorohydrin, azides, among others, which serve as attachment vehicles for coupling of biomolecules to substrate surfaces. For example, covalent attachment of biomolecules using water soluble carbodiimides is described by Hoffman et al., "Covalent Binding of Biomolecules to Radiation-Grafted Hydrogels on Inert Polymer Surfaces," *Trans. Am. Soc. Artif. Intern. Organs,* 18, 10–18 (1972); and Ito et al., "Materials for Enhancing Cell Adhesion by Immobilization of Cell-Adhesive Peptide," *J. Biomed. Mat. Res.,* 25, 1325–1337 (1991).

The addition of coupling molecules to the substrate surfaces of medical devices, however, can add instability to the surfaces and increase the prospect for burial of the attached biomolecule in the coupling layer. Coupling molecules can also create undesirable crosslinks between the biomolecules or create crosslinks between surface functional sites, thereby inhibiting attachment or destroying the biological properties of the biomolecules. The use of coupling molecules also tends to decrease the specificity for attachment of the biomolecule to the substrate surface, thereby losing conformational control over the attachment process.

Thus, what is needed are alternative methods for attaching biomolecules to the substrate surface of a medical device, particularly methods that do not require the use of coupling molecules.

SUMMARY OF THE INVENTION

The present invention provides an improved method for covalently attaching a material to a substrate surface such as the surface of a biomaterial. Specifically, the present invention provides a method for making a medical device having a biomolecule immobilized on a substrate surface. The method includes the steps of: combining a periodate with a material comprising a 2-aminoalcohol moiety to form an aldehyde-functional material; combining the aldehyde-functional material with a material comprising a primary amine moiety to bond the two materials together through an imine moiety; and reacting the imine moiety with a reducing agent to form an immobilized biomolecule on a medical device substrate surface through a secondary amine linkage.

The material comprising a 2-aminoalcohol moiety can be a biomolecule or a substrate surface of a medical device. The material comprising a primary amine moiety can also be a biomolecule or a substrate surface to which the biomolecule becomes attached.

Preferably, the method involves the steps of: combining a periodate with a biomolecule having a 2-aminoalcohol moiety to form an aldehyde-functional biomolecule in an aqueous solution having a pH of about 4–9 and a temperature of about 0°–50° C.; combining the aldehyde-functional biomolecule with a substrate surface comprising a primary amine moiety to immobilize the biomolecule on the substrate surface through an imine moiety; and reacting the imine moiety with a reducing agent to form an immobilized biomolecule on the substrate surface through a secondary amine linkage.

The method of the present invention can also be used to crosslink the molecules of a material comprising both a 2-aminoalcohol moiety and a primary amine moiety. The method includes the steps of: combining a periodate with the material to oxidize the 2-aminoalcohol moiety to form an aldehyde moiety; allowing the aldehyde moiety to combine with the amine moiety forming an imine moiety; and reacting the imine moiety with a reducing agent to form a secondary amine and a crosslinked material. Typically, the crosslinked molecules are crosslinked biomolecules.

A "biomaterial" may be defined as a material that is substantially insoluble in body fluids and that is designed and constructed to be placed in or onto the body or to contact fluid of the body. Ideally, a biomaterial will not induce undesirable reactions in the body such as blood clotting, tissue death, tumor formation, allergic reaction, foreign body reaction (rejection) or inflammatory reaction; will have the physical properties such as strength, elasticity, permeability and flexibility required to function for the intended purpose; can be purified, fabricated and sterilized easily; will substantially maintain its physical properties and function during the time that it remains implanted in or in contact with the body. The biomaterials suitable for use in the method of the present invention either include a 2-aminoalcohol moiety, an amine moiety, or both.

A "medical device" may be defined as a device that has surfaces that contact tissue, blood, or other bodily fluids in the course of their operation, which fluids are subsequently used in patients. This can include, for example, extracorporeal devices for use in surgery such as blood oxygenators, blood pumps, blood sensors, tubing used to carry blood and the like which contact blood which is then returned to the patient. This can also include endoprostheses implanted in blood contact in a human or animal body such as vascular grafts, stents, pacemaker leads, heart valves, and the like that are implanted in blood vessels or in the heart. This can also include devices for temporary intravascular use such as catheters, guide wires, and the like which are placed into the blood vessels or the heart for purposes of monitoring or repair.

DETAILED DESCRIPTION OF THE INVENTION

This invention is aimed at solving a number of problems associated with the use of medical devices. The invention involves an oxidative process for covalently attaching biomolecules to substrate surfaces, such as the surface of a biomaterial, for use in medical devices. The invention also provides an oxidative method for enhancing the biological and physical properties of the substrate or substrate coating.

Biomolecules that possess carbon-carbon bonds bearing an amine moiety adjacent to a hydroxyl moiety (i.e., a 2-aminoalcohol moiety) are oxidizable with periodate, which can be provided as periodic acid or salts thereof, such as sodium periodate, potassium periodate, or other alkali metal periodates. Typically, a stoichiometric amount of periodate is used to oxidize the 2-aminoalcohol moiety, although an excess could be used. Oxidation of such biomolecules forms reactive aldehyde moieties within the biomolecules.

The oxidation is carried out in an aqueous solution, preferably an aqueous buffered solution, at a temperature that does not destroy the biological properties of the biomolecule. Generally, buffers having a pH in a range of about 4–9 can be used, with a pH of about 6–8 desired for certain pH sensitive biomolecules. Generally, the oxidation is carried out a temperature of about 0°–50° C., and preferably at a temperature of about 4°–37° C. Depending on the biomolecule, oxidation reactions can be carried out for as short as a few minutes to as long as many days. Commonly, oxidation is complete within 24 hours. Long-term oxidation reactions are preferably performed in the dark to prevent "overoxidation."

Treatment times and temperatures for the oxidation process tend to be inversely related. That is, higher treatment temperatures require relatively shorter treatment times. The limitations of time and temperature are governed by the effect of the treatment on the biological stability of the biomolecule. Treatment conditions outside the above said ranges are still within the scope of this invention. There is a wide latitude in determining the proper conditions for a particular system and these conditions can be readily determined by one skilled in the art by routine experimentation upon a reading of the information presented herein.

Subsequent to oxidation, the reaction solution may be stored prior to attachment to a substrate at about 4° C. Typically, the storage stability of the reaction solution at a neutral pH or slightly acidic pH can extend for 1–14 days and sometimes even months when stored in the dark. Typically, the oxidation of the 2-aminoalcohol moiety can result in the formation of two different aldehyde-functional materials. If desired, these aldehyde-functional materials can be separated by a variety of known techniques based on affinity, molecular weight, etc.

The resultant aldehyde moieties interact with sites on a substrate surface for covalent attachment of the biomolecules. These substrate surface attachment sites comprise amine moieties, which react with aldehyde moieties forming imines. The substrate surface to which the biomolecule is to be coupled should contain an adequate density of amine moieties for attaching the desired number of biomolecules.

Substrates that do not contain amines on their surface can easily be aminated by a number of methods well known to those skilled in the art. For example, amines can be provided by plasma treating materials with ammonia gas as described by Holmes and Schwartz, "Amination of Ultra-high Strength Polyethylene using Ammonia Plasma," *Composites Science and Technology*, 38, 1–21 (1990). Alternatively, amines can be provided by grafting acrylamide to the substrate followed by chemical modification to introduce amine moieties by methods well known to those skilled in the art. Polyvinyl amines or polyalkylimines can also be covalently attached to polyurethane surfaces according to the method taught by U.S. Pat. No. 4,521,564 (Solomone et al.). Alternatively, for example, aminosilane can be attached to the surface as set forth in U.S. Pat. No. 5,053,048 (Pinchuk), a grafted acrylamide-containing polymer can be attached by radiation grafting as set forth in U.S. Pat. No. 3,826,678 (Hoffman et al.), a grafted N-(3-aminopropyl) methacrylamide-containing polymer can be attached by ceric ion grafting as set forth in U.S. Pat. No. 5,344,455 (Keogh et al.).

Typically, when an aldehyde moiety (RCH(O)) reacts with a primary amine moiety (—NH$_2$), an equilibrium is set up with the reaction product, which is a relatively unstable imine moiety (—N=CHR). This coupling reaction can be carried out under the same conditions described above for the oxidation, which are designed to protect the biomolecule from damage. To stabilize the linkage between the biomolecule and the substrate surface, subsequent reductive alkylation of the imine moiety is carried out using reducing agents (i.e., stabilizing agents) such as, for example, sodium borohydride, sodium cyanoborohydride, and amine boranes, to form a secondary amine (—NH—CH$_2$—R). This reaction can also be carried out under the same conditions described above for the oxidation. Typically, however, the coupling and stabilizing reactions are carried out in a neutral or slightly basic solution and at a temperature of about 0°–50° C. Preferably, the pH is about 6–10, and the temperature is about 4°–37° C., for the coupling and stabilizing reactions. These reactions (coupling and stabilizing) can be allowed to proceed for just a few minutes or for many hours. Commonly the reactions are complete (i.e., coupled and stabilized) within 24 hours.

Generally, biomolecules used according to this invention can be, for example: antibacterial and antimicrobial agents; anticoagulant and antithrombotic agents; platelet agents; anti-inflammatories; enzymes; catalysts; hormones; growth is factors; drugs; vitamins; antibodies; antigens; nucleic acids; dyes (which act as biological ligands); DNA and RNA segments; and proteins and peptides. The biomolecules can be synthetically derived or naturally occurring. As long as the biomolecules include carbon-carbon bonds bearing an amine moiety adjacent to a hydroxyl moiety, they can be attached to an aminated substrate surface by the method of the present invention. Specific examples of such biomolecules include proteins and peptides, synthetic or natural, which contain N-terminal serine, N-terminal threonine, or 5-hydroxylysine (5-hydroxylysine is only known to occur naturally in collagen, but in principal can be placed anywhere in a synthetic peptide or protein).

Some biomolecules are susceptible to conformational changes when brought into contact with a hydrophobic substrate surface. These conformational changes can lead to the exposure of internalized nonpolar groups which can lead to hydrophobic interactions between the biomolecule and the surface. These hydrophobic interactions can cause the exclusion of water molecules that normally surround the biomolecule in solution. This exclusion of water molecules between the biomolecule and the surface strengthens the hydrophobic interaction and can cause further conformational change of the biomolecule. The degree of conformational change a biomolecule experiences may or may not destroy its biological properties. Therefore, one must take into account the hydrophobic nature of the substrate surface when attaching biomolecules which are prone to hydrophobic interactions. In these cases, it is preferred to create a hydrophilic environment on the substrate surface, thereby preventing any unwanted hydrophobic interactions between the biomolecule and the surface which can destroy the biological properties of the biomolecule. There are a number of surface-derivatization techniques, e.g., grafting techniques, well known to those skilled in the art for creating hydrophilic substrate surfaces. For example, techniques based on ceric ion initiation, ozone exposure, corona discharge, UV irradiation and ionizing radiation ($^{60}$Co, X-rays, high energy electrons, plasma gas discharge) are known.

The substrates that can be modified by the method of the present invention include metals such as titanium/titanium alloys, TiNi (shape memory/super elastic), aluminum oxide, platinum/platinum alloys, stainless steels, MP35N, elgiloy, haynes 25, stellite, pyrolytic carbon, silver or glassy carbon; polymers such as polyamides, polycarbonates, polyethers, polyesters, polyolefins including polyethylenes or polypropylenes, polystyrenes, polyurethanes, polyvinyl chlorides, polyvinylpyrrolidones, silicone elastomers, fluoropolymers, polyacrylates, polyisoprenes, polytetrafluoroethylenes, and rubber; minerals or ceramics such as hydroxapatite; human or animal protein or tissue such as bone, skin, teeth, collagen, laminin, elastin or fibrin; organic materials such as wood, cellulose, or compressed carbon; and other materials such as glass, or the like. Substrates made using these materials can be coated or uncoated, and derivatized or underivatized.

The method of the invention can be used to modify substrates of any shape or form including tubular, sheet, rod and articles of proper shape. Preferably, the substrate is a biomaterial for use in a number of medical devices such as vascular grafts, aortic grafts, arterial, venous, or vascular tubing, vascular stents, dialysis membranes, tubing, or connectors, blood oxygenator tubing or membranes, ultrafiltration membranes, intra-aortic balloons, blood bags, catheters, sutures, soft or hard tissue prostheses, synthetic prostheses, prosthetic heart valves, tissue adhesives, cardiac pacemaker leads, artificial organs, endotracheal tubes, lenses for the eye such as contact or intraocular lenses, blood handling equipment, apheresis equipment, diagnostic and monitoring catheters and sensors, biosensors, dental devices, drug delivery systems, or bodily implants of any kind.

Although the method of the invention has been described using aminated substrates and biomolecules containing 2-aminoalcohol moieties, it will be understood by one of skill in the art that the opposite could be done. That is, aminated (i.e., amine-containing or amino-functional) biomolecules can be covalently attached to a substrate surface having 2-aminoalcohol moieties using the method of the present invention. Substrates that do not contain an adequate number of oxidizable attachment sites (i.e., 2-aminoalcohol moieties) can easily be derivatized by a number of methods well known to those skilled in the art.

It will also be understood by one of skill in the art that substrates or substrate coatings can be crosslinked using the method of the present invention. That is, substrates or substrate coatings that contain both primary amine moieties and 2-aminoalcohol moieties can be crosslinked to provide desired physical and biological properties. The resultant imines formed following the crosslinking of the aldehydes (as a result of oxidation of the 2-aminoalcohol moieties) and amines contained within the substrate or substrate coating can be stabilized using a reducing agent as described above. For example, structural proteins and tissues can be crosslinked to form a material that can be used as a substrate or a substrate coating. Also, biomolecules, as described herein, can also be attached to the crosslinked material.

An example of a material that can be used in all aspects of the present invention is collagen. Collagen, which is found in connective tissue, has special amino acids, one of which is 5-hydroxylysine, which can be oxidized with a source of periodate to form a pendant aldehyde moiety. The resultant aldehyde moieties can be used to crosslink the collagen through bonds formed between the aldehydes and nearby lysine residues contained within the collagen. The resultant imine bonds can then be reduced using a mild reducing agent like sodium borohydride, sodium cyanoborohydride, or amine boranes. These crosslinks can endow collagen and/or tissue with desirable biological and/or physical properties such as mechanical strength, anti-immunogenicity, biostability, among others, without the use of a coupling agent. Thus, the method of the present invention eliminates the need for using glutaraldehyde, a commonly used cytotoxic coupling agent, to crosslink the collagen molecules to control its physical and biological properties.

The aldehyde moieties formed by oxidation of collagen can also be used to couple a variety of amine-containing biomolecules to a collagen substrate. Also, the ability to create aldehyde moieties along collagen molecules enables them to be covalently attached to amine containing substrate surfaces. Such collagen-coated substrate surfaces can be used, for example, as cell seeding surfaces, cell binding surfaces, cell separating surfaces, tissue fixation, collagen-coated stents or collagen-coated vascular grafts.

Although the examples described below involve treatment on polymeric films or tissue culture plates as the substrate surfaces, it is not intended that this invention be so limited.

EXAMPLE 1

Periodate Oxidation Of A Peptide Containing An N-Terminal Serine

A tripeptide made of three serine amino acids and a dipeptide made of two lysine amino acids, both obtained from Sigma Chemical Co. (St. Louis, Mo.), were incubated in sodium metaperiodate (NaIO$_4$) also obtained from Sigma Chemical Co. (St. Louis, Mo.). The tripeptide, 0.90 mmoles, was incubated in the dark while shaking at room temperature for 3 hours in 10 ml deionized water containing 1.2 mmoles NaIO$_4$. The resultant solution, 2.5 µl, was added to 2 ml of a solution containing 0.8 g NaOH, 0.2 g 4-amino-3-hydrazino-5-mercapto-1,2,4triazole, which is available under the trade designation PURPALD from Sigma Chemical Co. (St. Louis, Mo.), in 20 ml deionized water, and shaken vigorously for 15 minutes at room temperature. The dipeptide, 0.72 mmoles, was incubated in the dark while shaking at room temperature for 3 hours in 10 ml deionized water containing 1.2 mmoles NaIO$_4$. The resultant solution, 10 µl (note that this amount is four times the amount used for the tripeptide), was then added to 2 ml PURPALD solution and shaken vigorously for 15 minutes at room temperature. The resultant solutions were then analyzed spectrophotometrically at 550 nm. Dickinson and Jacobsen, *Chem.*

Commun., 1719 (1970), described the specific and sensitive reaction of aldehydes with PURPALD to yield purple-to-magenta-colored 6-mercapto-5-triazolo-(4,3-b)-s-tetrazines which can be measured spectrophotometrically at 550 nm. Sample absorbances obtained at 550 nm were 0.04 for the dipeptide and 1.81 for the tripeptide, which indicates that only the tripeptide which contained an N-terminal serine was successfully oxidized using periodate. The dipeptide of the two lysine amino acids lacked a moiety with carbon-carbon bonds bearing an amine moiety adjacent to a hydroxyl moiety.

EXAMPLE 2

Periodate Oxidation Of A Peptide Containing An N-Terminal Threonine

A dipeptide made of N-terminal threonine and leucine amino acids obtained from Sigma Chemical Co. (St. Louis, Mo.) was incubated in sodium metaperiodate ($NaIO_4$) also obtained from Sigma Chemical Co. (St. Louis, Mo.). The dipeptide, 4.3 mmoles, was incubated in the dark while shaking at room temperature for 3 hours in 10 ml deionized water containing 1.2 mmoles $NaIO_4$. The resultant solution, 10 µl, was added to 2 ml of the PURPALD solution described in Example 1 and shaken vigorously for 15 minutes at room temperature. After the 15 minutes of shaking at room temperature, the resultant solution was analyzed spectrophotometrically at 550 nm. Sample absorbance obtained at 550 nm was 0.62 indicating the periodate had successfully oxidized the N-terminal threonine amino acid present in the dipeptide.

EXAMPLE 3

Periodate Oxidation Of A Peptide Containing An N-Terminal Serine

A pentapeptide made of N-terminal serine, aspartic acid, glycine, arginine, and glycine amino acids obtained from Sigma Chemical Co. (St. Louis, Mo.) was incubated in sodium metaperiodate ($NaIO_4$) also obtained from Sigma Chemical Co. (St. Louis, Mo.). The pentapeptide, 0.01 mmoles, was incubated in the dark while shaking at room temperature for 3 hours in 2 ml deionized water containing 0.23 mmoles $NaIO_4$. The resultant solution, 10 µl, was added to 2 ml of the PURPALD solution described in Example 1 and shaken vigorously for 15 minutes at room temperature. After the 15 minutes of shaking at room temperature, the resultant solution was analyzed spectrophotometrically at 550 nm. Sample absorbance obtained at 550 nm was 0.74, which again indicates periodate had successfully oxidized the N-terminal serine amino acid present in the pentapeptide.

EXAMPLE 4

Oxidation Of Collagen

Mouse collagen, type IV, obtained from Sigma Chemical Co. (St. Louis, Mo.) was oxidized with sodium metaperiodate ($NaIO_4$). Collagen type IV is known to mediate the attachment of epithelial, endothelial, myoblasts and nerve cells in vivo and in vitro. Two collagen solutions were prepared by i) mixing half a vial of collagen with 56 mg $NaIO_4$ in 5 ml deionized water and ii) mixing half a vial of collagen in 5 ml deionized water. Both solutions were incubated in the dark for 2 hours while shaking at room temperature. The resultant solutions, 100 µl of each, were added to 2 ml the PURPALD solution described in Example 1 and shaken vigorously for 30 minutes at room temperature. After the 30 minutes of shaking at room temperature, the resultant solutions were analyzed spectrophotometrically at 550 nm. The PURPALD solution was used as the blank. Sample absorbances obtained at 550 nm were 0.03 for nonoxidized collagen and 0.25 for oxidized collagen, which indicates that the collagen was oxidized forming aldehyde moieties.

EXAMPLE 5

Attachment Of Periodate Oxidized Biomolecules To Aminated Substrates

One technique for creating amines on substrate surfaces entails grafting substrate surfaces with acrylamide (AAm) and N—(3-aminopropyl)methacrylamide (APMA) monomers using ceric ($Ce^{IV}$) ions. The $Ce^{IV}$ ions create free radicals on ozone treated silicone and polystyrene surfaces and untreated polyurethane surfaces which initiate the graft copolymerization of the acrylamides. The amount of surface amination (the graft copolymerization of APMA and AAm) that takes place on the substrate surface can be measured via staining with ponceau S dye, a negatively charged dye molecule. This dye ionically associates with the primary amines on the aminated surface. Following grafting, a periodate oxidized biomolecule can be coupled to the amine containing derivatized substrate surface. The 2-aminoalcohol-containing biomolecule is first oxidized with sodium metaperiodate ($NaIO_4$) forming reactive aldehyde moieties. These aldehyde moieties are then used to covalently attached fibronectin to the primary amino moieties present on the substrate surface. Sodium cyanoborohydride ($NaCNBH_3$) is then used to stabilize the imine linkages. Specific procedures required for each of these steps are described below.

Polystyrene 24 well tissue culture plates were ozone treated by placing the culture plates in an ozone reaction vessel for 30 minutes while oxygen, which contained ozone, was flowing at a rate of 1.3 $cm^3$/min. The oxygen containing ozone was created by flowing the oxygen through a corona discharge apparatus, which exposed the flowing oxygen to an 8000 V electrical potential. Following ozone treatment, the plates were soaked in nitrogen purged deionized water for 30 minutes at room temperature. Following the 30 minute soak in nitrogen purged deionized water, the plates were grafted with acrylamide (AAm) and N—(3-aminopropyl)methacrylamide (APMA) monomers using $Ce^{IV}$ ion. The grafting solution consisted of 40 g AAm, 10 g APMA, 50 g deionized water solution, and 20 g $Ce^{IV}$ ion solution. The $Ce^{IV}$ ion solution consisted of 2.74 g ceric ammonium nitrate and 3.15 g nitric acid in 50 ml deionized water. The plates were allowed to graft for 3 hours in a 65° C. nitrogen purged oven. Following grafting the plates are rinsed vigorously with deionized water. The grafted plates were then tested with ponceau S dye. Following staining, the ponceau S dye was released from the surface using a 1% sodium dodecyl sulphate (SDS) solution and quantified spectrophotometrically at 520 nm. Sample absorbances obtained at 520 nm were 0.00 for nonderivatized plates and 1.44 for surface-derivatized plates. As the results demonstrate, the surface-derivatized plates contain primary amines on their surfaces.

The 2-aminoalcohol moiety of a peptide can be oxidized using the procedure of Example 1. Sodium cyanoborohydride (1 mg/ml) then is added to the oxidized peptide solution. The resultant solution then is immediately added to each of the amine containing surface-derivatized tissue culture plate wells (approximately 1 ml solution/well). The oxidized peptide is then incubated in the derivatized tissue culture plate wells overnight at room temperature. Following incubation, the wells are vigorously rinsed with phosphate buffered saline (PBS) solution.

Polyurethane film samples were cut into 1.4 cm diameter disks. Sample disks were grafted with Aam and APMA monomers using $Ce^{IV}$ ion. The sample disks were allowed to graft 1 hour at room temperature. Following grafting, the sample disks were rinsed vigorously with deionized water. Again, the 2-aminoalcohol moiety of a peptide can be oxidized as previously described. Sample disks are then exposed to the oxidized peptide solution. Sodium cyanoborohydride is then added (1 mg/ml) and the resultant solution and sample disks are incubated overnight at room temperature. Following incubation, the polyurethane sample disks are vigorously rinsed with PBS.

It will be appreciated by those skilled in the art that while the invention has been described above in connection with particular embodiments and examples, the invention is not necessarily so limited and that numerous other embodiments, examples, uses, modifications and departures from the embodiments, examples and uses are intended to be encompassed by the claims attached hereto. The entire disclosure of each patent and publication cited herein is incorporated by reference, as if each were individually incorporated by reference.

What is claimed is:

1. A method of crosslinking a coating on a surface of a medical device, the coating imparting improved biocompatibility characteristics to the surface, the surface being suitable for contacting tissue or blood, the method comprising the ordered steps of:

(a) producing on the surface a coating comprising a 2-aminoalchol moiety and an amine moiety;

(b) applying a periodate to the coating to oxidize the 2-aminoalcohol moiety to form an aldehyde moiety;

(c) allowing the aldehyde moiety to combine with the amine moiety to form an imine moiety; and (d) reacting the imine moiety with a reducing agent to form an amine linkage and thereby cause at least portions of the coating to crosslink.

2. The method of claim 1 wherein the periodate comprises at least one of periodic acid, and alkali metal periodates.

3. The method of claim 1 wherein the reducing agent comprises at least one of sodium borohydride, sodium cyanoborohydride and amine borane.

4. The method of claim 1 wherein the periodate is combined with the 2-aminoalcohol moiety in an aqueous solution having a pH between about 4 and about 9.

5. The method of claim 1 wherein the periodate is combined with the 2-aminoalcohol moiety in an aqueous solution having a temperature between about 0 degrees Celsius and about 50 degrees Celisius.

6. The method of claim 1 wherein at least a portion of the surface forms at least one of a tube, a rod, a membrane, a balloon, a bag and a sheet.

7. The method of claim 1 wherein the surface comprises a biocompatible material selected from the group consisting of metal, titanium, titanium alloys, tin-nickel alloys, shape memory alloys, aluminum oxide, platinum, platinum alloys, stainless steel, MP35N stainless steel, elgiloy, stellite, pyrolytic carbon, silver carbon, glassy carbon, polyamide, polycarbonate, polyether, polyester, polyolefin, polyethylene, polypropylene, polystyrene, polyurethane, polyvinyl chloride, polyvinylpyrrolidone, silicone elastomer, fluoropolymer, polyacrylate, polyisoprene, polytetrafluoroethylene, rubber, ceramic, hydroxapatite, human protein, human tissue, animal protein, animal tissue, bone, skin, teeth, collagen, laminin, elastin, fibrin, wood, cellulose, compressed carbon and glass.

8. The method of claim 2 wherein the alkali metal periodates comprise at least one of sodium periodate and potassium periodate.

9. A method of forming a coating on a surface of a medical device, the coating imparting improved biocompatibility characteristics to the surface, the surface being suitable for contacting tissue or blood , the method comprising the ordered steps of:

(a) providing the medical device, the device having a suitable biomaterial forming the surface, a 2-aminoalcohol moeity being disposed on the surface;

(b) combining a periodate with the 2-aminoalcohol moiety, the periodate oxidizing the 2-aminoalcohol moiety and thereby forming an aldehyde-functional moiety disposed on the surface;

(c) combining the aldehyde-functional moiety with an amine moiety to bond the aldehyde-functional material to the amine moiety and thereby form an imine moiety; and (d) reacting the imine moiety with a reducing agent to form the coating, the coating being immobilized on the surface by an amine linkage.

10. The method of claim 9 wherein the oxidizing step is performed in the absence of light.

* * * * *

UNITED STATES PATENT AND TRADEMARK OFFICE
CERTIFICATE OF CORRECTION

PATENT NO. : 5,821,343
DATED : Oct. 13, 1998
INVENTOR(S) : James R. Keogh

It is certified that error appears in the above-identified patent and that said Letters Patent is hereby corrected as shown below:

On the title page, insert the following item:

"[73] Assignee: Medtronic, Inc., Minneapolis, Minn."

Signed and Sealed this

Twenty-fifth Day of April, 2000

Attest:

Q. TODD DICKINSON

*Attesting Officer*  *Director of Patents and Trademarks*